(12) United States Patent
Downer et al.

(10) Patent No.: US 7,282,168 B2
(45) Date of Patent: Oct. 16, 2007

(54) GAS SENSOR ASSEMBLY AND METHOD

(75) Inventors: Anthony Charles Downer, Hants (GB); John Chapples, Hampshire (GB); Andrew Peter Millar, Hants (GB)

(73) Assignee: City Technology Limited, Portsmouth (GB)

( * ) Notice: Subject to any disclaimer, the term of this patent is extended or adjusted under 35 U.S.C. 154(b) by 490 days.

(21) Appl. No.: 10/258,560

(22) PCT Filed: Apr. 26, 2001

(86) PCT No.: PCT/GB01/01862

§ 371 (c)(1),
(2), (4) Date: Feb. 24, 2003

(87) PCT Pub. No.: WO01/81911

PCT Pub. Date: Nov. 1, 2001

(65) Prior Publication Data

US 2003/0168336 A1    Sep. 11, 2003

(30) Foreign Application Priority Data

Apr. 26, 2000  (GB) .................................. 0010180.8

(51) Int. Cl.
*G01N 27/404* (2006.01)
(52) U.S. Cl. .................. 264/255; 264/279; 204/431
(58) Field of Classification Search ................ 204/430, 204/431; 29/888.3; 264/255, 267, 279
See application file for complete search history.

(56) References Cited

U.S. PATENT DOCUMENTS

| 2,666,805 A | 1/1954 | Smith |
| 2,864,883 A | 12/1958 | Townsend |
| 3,604,641 A * | 9/1971 | Wilson et al. .............. 241/301 |
| 3,902,970 A | 9/1975 | Levin |
| 3,997,419 A | 12/1976 | Scott et al. |
| 4,072,578 A * | 2/1978 | Cady et al. .............. 435/287.1 |
| 4,251,432 A * | 2/1981 | Martin .................. 523/205 |
| 4,410,479 A * | 10/1983 | Cyriax .................. 264/255 |
| 4,983,344 A * | 1/1991 | Brown .................. 264/255 |
| 5,271,880 A * | 12/1993 | Lindsay .................. 264/219 |
| 5,702,576 A | 12/1997 | Kiesele et al. |
| 5,914,019 A | 6/1999 | Dodgson et al. |

FOREIGN PATENT DOCUMENTS

| DE | 19728370 A1 | 1/1999 |
| EP | 0239297 | 9/1987 |
| GB | 0 239 297 A2 | 9/1987 |

OTHER PUBLICATIONS

Communication from corresponding EPO application. 01923841.9-1240; date Jun. 7, 2005.

* cited by examiner

*Primary Examiner*—Kaj K. Olsen
(74) *Attorney, Agent, or Firm*—James B. Conte; Barnes & Thornburg LLP (57) ABSTRACT

A gas sensor assembly comprises a housing (65) including a bore (61). A pin (50) extends through the bore (61) and an O-ring (100) is located in the bore. The O-ring (100) contacts the pin (50) and parts of the bore (61) so as to be restrained against movement in both lateral and axial directions. Two- and three-shot molding processes are described for fabricating the assembly.

26 Claims, 5 Drawing Sheets

GAS SENSOR ASSEMBLY AND METHOD

This application is a 371 of PCT/GB01/01862 filed Apr. 26, 2001. This application claims priority from UK Application 0010180.8, filed Apr. 26, 2000.

The invention relates to a gas sensor assembly and a method for manufacturing a seal assembly for a gas sensor assembly.

BACKGROUND OF THE INVENTION

There are a variety of gas sensor constructions in which it is necessary to seal a member such as a pin or the like into a bore so as to prevent the passage of liquid or gas through the bore. O-rings have been used in the past to achieve such sealing both in cases where the components move relative to one another (such as described in U.S. Pat. No. 4,221,651) and in which they are relatively static. The present invention is concerned with a static arrangement of components.

The method of securing O-rings in a static sealing configuration recommended by manufacturers is to place the ring in a U-shaped recess extending around the bore so that the ring contacts the elongate member and the seal action is based on the ability of the seal to undergo axial or radial deformation of its cross-section. In order for the seal to function properly, manufacturers require that the size of the groove or channel is larger than the O-ring cross-section typically having a cross-sectional area more than 25% that of the O-ring so that the pressure can act on a relatively large part of the ring surface and so that there is sufficient space in the groove should any volume increase of the O-ring occur due to exposure to chemicals.

We have found, however, that some leakage of liquid still occurs in these configurations.

BRIEF SUMMARY OF THE INVENTION

In accordance with a first aspect of the present invention, a gas sensor assembly comprises a housing containing gas sensing components; a member secured to the housing; and an annular seal supported by the housing in contact with the member and parts of the housing so as to be restrained against movement in both lateral and both axial directions.

We have undergone detailed investigations into the use of annular seals such as O-rings in these static situations and we have realized that one problem that can occur in certain applications is that if the fluid pressure reduces, then the seal will relax to an extent dependent upon the elastic properties of the material. Furthermore, in certain applications such as electrochemical gas sensors, there may well be no pressure exerted by the retained liquid (the electrolyte). However, by virtue of the nature of the assembly, the joints between the mating surfaces act as capillary channels allowing the liquid to wick up into the seal area. Thus, the region around the seal quickly becomes bathed in liquid such as acid under conditions where the seal itself is not necessarily under compression. Thus, the possibility of leakage is increased.

Our solution is to ensure that the seal is restrained on all four sides and is preferably stressed or always under compression whatever the fluid pressure and thus the seal condition is maintained.

The invention can be used in a wide variety of situations in which seals against gases and/or liquids are required. It is particularly useful where the member is an electrical connector located in a bore but is also applicable to seal other components such as a gas filter top.

In addition, the invention is applicable to a wide variety of gas sensors such as electrochemical, pellistor, infrared or calorimetric gas sensors. For example, infrared devices have O-rings around their gas chambers, and calorimetric sensors with two part housings which clip together, to restrain a filter membrane via an O-ring. Pellistor housings involving O-ring seals are also known.

The invention is of particular benefit when used with an electrochemical gas sensor of the kind comprising sensing and counter electrodes and intervening electrolyte located within a housing. The electrodes are electrically connected to respective connectors extending through bores in the housing to which they are sealed.

The connectors provide an electrical connection between (a) the internal electrode and associated current collection means and (b) the external circuit where the sensor output is measured and processed. Additionally, such connectors may be used to allow potentiostatic control of the sensor electrode operating potential via appropriate circuits. Connectors used in this application require relatively high conductivity (to limit any IR losses between the sensor and the indicating/controlling circuitry). Suitable materials include platinum and gold, often in the form of coatings on nickel or steel components, graphite (in rod form), and metal coated and/or plated polymerics.

These connector components may be in the form of, for example, pins, pads, wires, ribbons, etc.

An important aspect in the construction of these sensors is the prevention of leakage of electrolyte. This is particularly important in the case of oxygen sensors which employ liquid electrolyte, usually in the form of strongly alkaline liquid. Any minor defect in the sensor represents a potential leakage path. In particular, it is well known that the electrical connections through the housing are frequently the sources of electrolyte leakage.

In comparatively large sensors where minimisation of internal volume is not a primary design requirement, it is common to incorporate a double-walled construction method, so that the connectors pass through the sensor body in a region which is already isolated from the electrolyte reservoir. Under such circumstances, the constraints placed upon the connector/body seal, whilst significant, are relatively easily managed.

However, in sensors where internal volume is at a great premium (for example in metal-air oxygen sensors where the device lifetime is fundamentally dictated by the volume of consumable lead incorporated), it is generally not possible to employ a double-walled method of construction. In these circumstances, the longevity and reliability of the connector/body seal are critical.

A typical example of a known construction makes use of a connector pin which passes through a moulded polymer sensor housing in an area containing an aggressive liquid electrolyte (which may be an acid or alkaline material). Current design and production methods usually rely on the interference fit of the connector into the housing in order to provide both mechanical fixation and an hermetic seal, thereby preventing the transport or migration of electrolyte from within the sensor body (i.e. leakage).

The main shortcomings of this technique are that due to
strain acceptance limits,
differing coefficients of thermal expansion,
the effect of mould processing upon the polymer characteristics, and
ageing characteristics of the differing materials involved (leading to creep), the properties of the hermetic seal are not consistent. Therefore, leakage is generally not particularly well controlled and may cause premature cell failure and/or external contamination with electrolyte.

In other examples, a barb can be added to the pin to assist in its retention once the initial insertion has been made. This can be important where, for example, the pin is pushed into and removed from sockets on connector boards which might tend to withdraw the pin from the sensor itself. As one increases the size of the barbs beyond that which can be readily forced through a given bore, it is also a natural step to utilize "hot insertion" processes, where thermal and/or ultrasonic methods (for example) are used to cause local heating of the sensor housing which then cools and re-seals around the pin and barb. However, none of these additional steps are in themselves sufficient to guarantee leakproof seals.

Consequently, the invention is particularly suited to overcome these problems with electrochemical gas sensors.

In some cases, the annular seal is unstressed but in the preferred arrangement the seal is stressed in at least one and preferably all lateral and axial directions.

The annular seal may be made of (natural) rubber but can advantageously employ a wide range of suitably compliant materials. In various circumstances, silicones, (thermoplastic) elastomers, polymers, PTFE, soft metals etc. might all be selected on the grounds of particular properties (e.g. chemical resistance, deformability, temperature behaviour, etc.).

The seal is typically an O-ring, either of the conventional type having a circular cross-section when relaxed or a non-circular cross-section as described below.

Additional sealing may be achieved by utilizing a cured potting compound compatible with the fluid to be used, the housing and elongate member materials.

We have found that using a suitable potting material, particularly if it is thermally or optically, eg UV, curable, significantly increases the integrity of the seal.

This aspect of the invention, however, is applicable to any potting compound with properties which render it physically (e.g. through thermal expansion etc. ) and chemically (i.e. resistant to attack, not corrosive) compatible with the liquid, elongate member and housing materials. Sealing on the outside of the housing is preferably employed, but in principle this could also (or alternatively) be done inside the housing. Although shadowing may be a problem in the case of light-cured materials, photoinitiated cationic compounds, where light is used to commence the reaction which then proceeds unaided, are now being considered for such applications. These do not suffer from significant shadowing.

In electrochemical gas sensors, the use of gelled electrolyte in place of a liquid has been proposed to further reduce the risk of electrolyte leakage. In such cases, the electrolyte is immobilised within a suitable gelling agent in order to reduce the free liquid volume within the casing.

The gelling reaction may take place in situ i.e. by placing the reactants in the housing and then running the entire assembly through an appropriate thermal curing cycle. However, some ungelled liquid tends to remain within the sensor, and the whole sensor assembly is subjected to thermal stresses which are typically at the extremes of the recommended operating range and may even be outside the specified operating conditions. The use of "pre-gelled" electrolyte, which is mixed with the gelling agent prior to introduction into the sensor minimizes the free liquid volume and obviates the need for thermal cycling of the sensor hardware.

However, experience shows that the use of gel does not allow any compromise in the efforts taken to provide good seals in regions where the electrolyte comes into contact with members passing through the sensor body. Indeed, given the requirement for equally robust seals irrespective of the presence or absence of gelling agents, sensor manufacturing processes may actually be simplified by using liquid electrolytes. All these options are open to the sensor designer.

Another reason why leakage can occur in seal assemblies of this type is due to the number of components involved and therefore we provide in accordance with a second aspect of the present invention, a method of manufacturing a seal assembly for a gas sensor assembly, the seal assembly comprising a housing to which a member is secured in use; and an annular seal supported by the housing, the method comprising moulding the housing and seal in separate injection moulding shots, such that the seal contacts the member in use so as to seal the bore against the passage of fluid.

In this aspect of the invention, instead of providing the seal as a separate component, it is pre-moulded into the housing. Thus, the component count is being reduced which not only assists in reducing the leakage problem but also simplifies assembly. As with the first aspect of the present invention, preferably the seal is located in an annular, generally U-shaped recess opening into the housing and contacts opposed sides of the recess and the side of the recess opposite the member. The term "U-shaped" is to be read broadly and to include laterally opening recesses being a variety of cross-sections such as square, rectangular, hyperbolic, etc.

Most preferably, the seal is stressed in at least one, preferably all, lateral and axial directions.

A further advantage of this method is that the seal may be chemically bonded to the housing thus significantly improving the seal and avoiding capillary leakage. Some overall compression of the seal is generally desirable which, where the seal surrounds a bore, could be achieved by providing the seal slightly proud of the bore. However, this compression is likely to be significantly less than that required to form a conventional seal in order to provide the required integrity.

Typically, the housing is moulded before the seal. However, in an alternative approach, the seal is moulded around the member in a first shot; and the housing is moulded around the seal and member in a second shot.

Furthermore, in accordance with a third aspect of the present invention, we provide a method of manufacturing a seal assembly for a gas sensor assembly, the seal assembly comprising a housing to which a member is secured in use, and an annular seal supported by the housing, the method comprising injection moulding the housing about the seal.

For example, a sensor housing could be moulded around a free standing, annular seal.

The method can be extended when the member is elongate and sealed in a bore of the housing to a three shot process in which in a third shot an additional seal is moulded into the bore.

The same or different, usually plastics, materials may be used in each moulding shot. Typically, the seal is fabricated from a thermoplastic elastomer (TPE) while the housing is made from another polymer.

The use of two-shot moulding/TPEs allows the generation of a separate seal via radial compression of the TPE. The use of a three-shot moulding technique offers additional benefits by virtue of the fact that some TPEs offer favorable sealing properties to metals (e.g. a pin connector) whereas others are to be preferred for use on polymer surfaces. Thus, a three-shot moulding method potentially allows a complex seal to be fabricated using a sandwich or layered structure where, in the case of an electrochemical gas sensor, the critical electrolyte seal is fabricated using materials optimised for the contacting surfaces.

The moulded seal is typically in the form of an O-ring but other forms of seal may be used. Seals with a variety of more complex footprints (e.g. a car head gasket) and cross-sectional forms (e.g. "lobed" O-rings or "wiping" seals) could be used.

It will be appreciated that the invention is applicable to two, three, four or more electrode electrochemical gas sensors. Furthermore, typically the housing will provide controlled gas access to the sensing electrode, for example by incorporating a gas phase, Knudsen, or solid state diffusion barrier.

Some examples of electrochemical gas sensors and methods for their assembly according to the present invention will now be described with reference to the accompanying drawings, in which:—

DETAILED DESCRIPTION OF THE INVENTION

Figure 1:
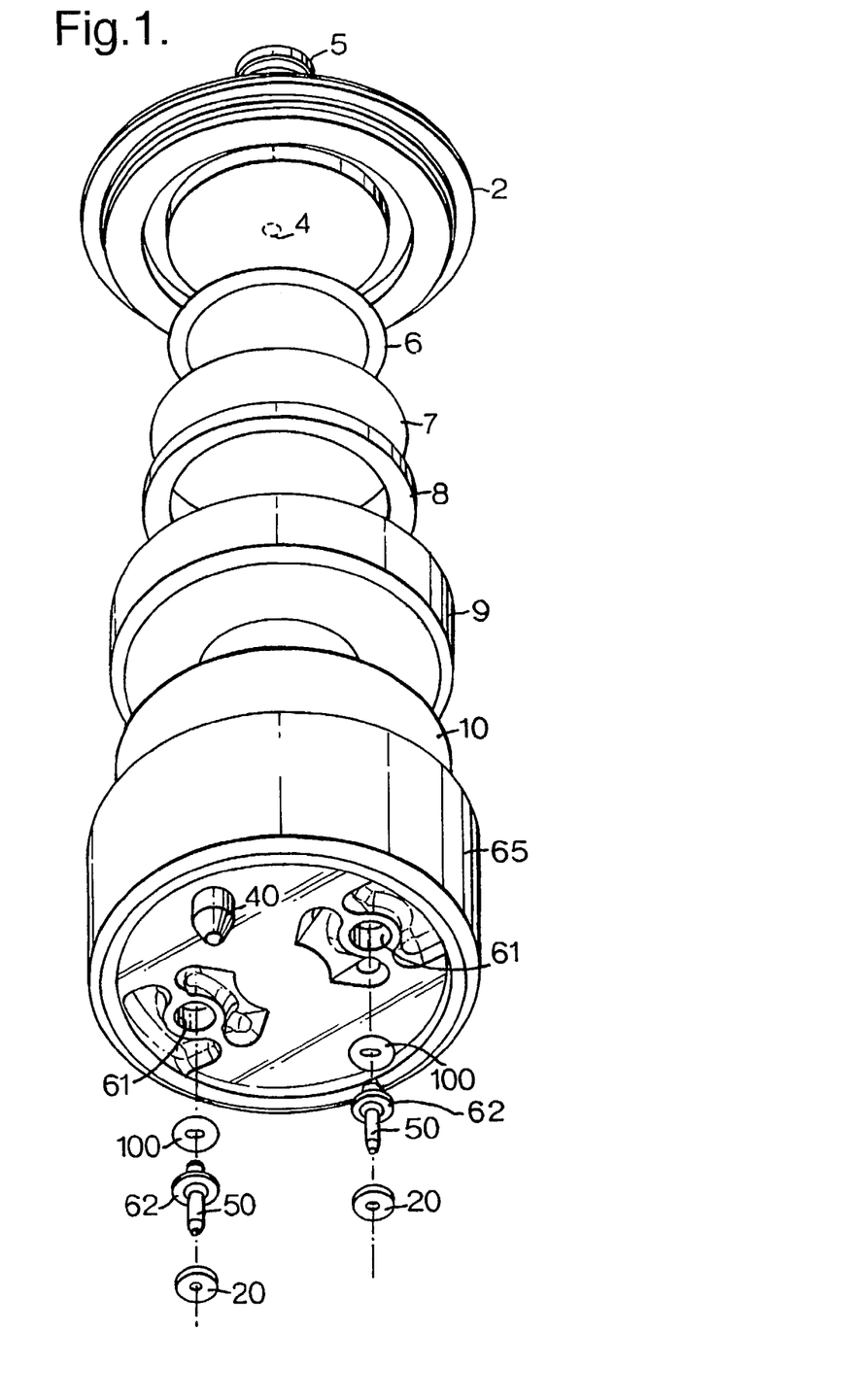
FIG. 1 is an exploded view of a sensor assembly.

FIG. 1 illustrates the primary components of a sensor assembly including a main housing component 65 which, following assembly, is bonded by welding or the like to a top housing component 2. The top housing component includes a central capillary hole 4 extending through it (which forms a gas phase diffusion barrier), a filter 5 being located in alignment with the hole 4. A sensing electrode 6 is located below the capillary hole 4. Below the sensing electrode 6 is a separator 7 and an O-ring 8. A counter electrode in the form of a lead anode 9 is positioned beneath the O-ring 8 and sits on a floor seal 10. It will be appreciated that several components have been omitted from FIG. 1 for clarity and indeed the construction of the assembly shown in FIG. 1 is conventional apart from the pin mountings which are to be described below.

The sensing electrode 6 and the counter electrode 9 are each connected to respective conductors (not shown) which are in turn connected to respective pins 50 which protrude through holes 61 in the base of the housing component 65. As will be described in more detail below, the pins 50 are secured in the holes 61 partly by a friction fit and partly by epoxy potting material 20. They are also sealed to the holes 61 via O-rings 100.

A dummy pin 40 extends from the base of the housing component 65 to assist in locating the sensor on a support member.

Figure 2:
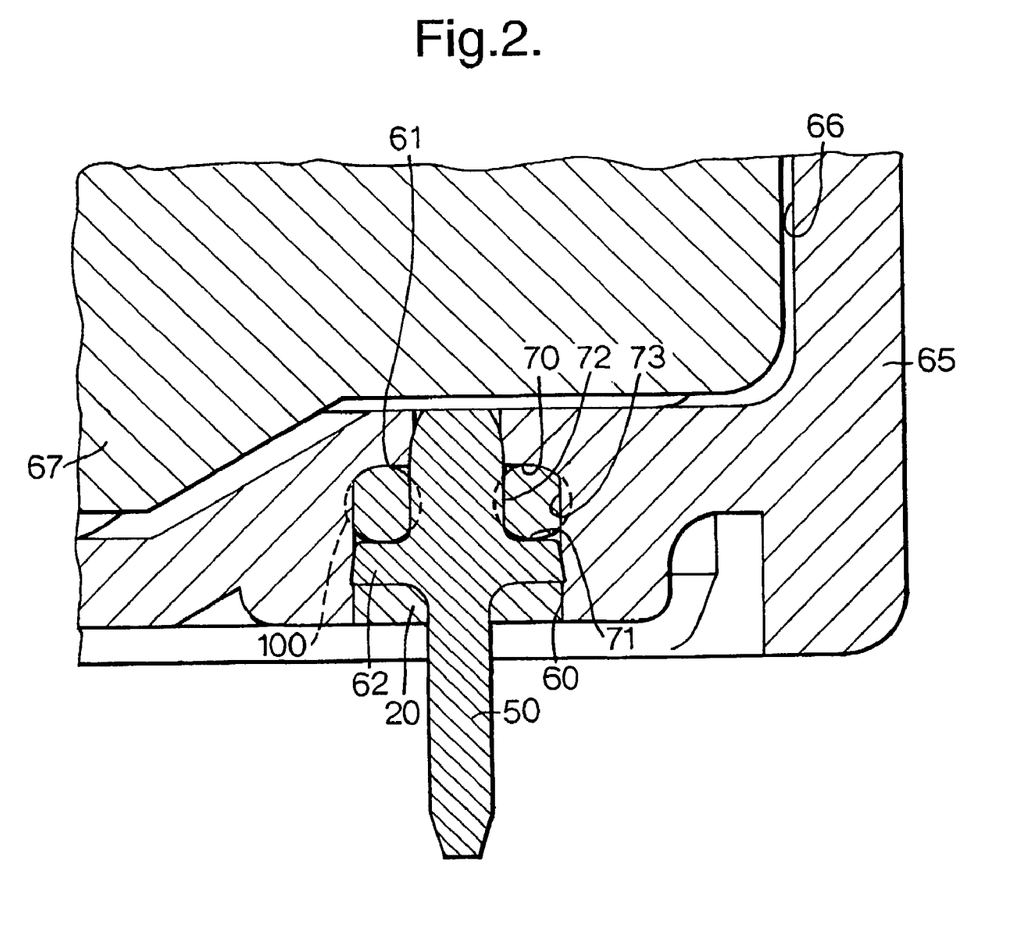
FIG. 2 is a cross-section through part of the housing of the sensor shown in FIG. 1.

FIG. 2 illustrates an example of the invention in which a T-shaped connector pin 50 is secured in a widened part 60 of the bore 61 extending through the base of the housing component 65. This securement is achieved partly by means of an interference fit between a lateral flange 62 integrally formed with the rest of the pin 50 with the surface of the bore 60 and partly by means of a potting material 20 which fills part of the space within the widened part of the bore 60. After inserting the pin 50 into the bore 61, the widened part of the bore 60 is filled with the potting material, such as an epoxy, which is then cured under UV radiation.

The electrolyte reservoir 66 defined by the housing part 65 is then provided with a consumable lead anode 67 which is saturated in electrolyte. This could be in liquid form, in which case it will be largely wicked into the compressed body of the lead wool ball by capillary action but with the possibility of some seepage of liquid. Alternatively, the electrolyte might be either pre- or post-gelled, in which case it would be more robustly held within the cavities formed by the intertwined strands of lead wool. The pre-gelled electrolyte is a liquid electrolyte with suitable additives that cause the material to "gel" by application of heat, thus reducing the amount of free liquid by a significant degree. The electrolyte is "gelled" in the lead anode 9 prior to assembly of the anode into the sensor to minimise both heat cycle stresses on the sensor, and the free liquid electrolyte inside the sensors.

The polymer preferably, although not exclusively, comprises units derived from polyacrylamides as is known in the art.

Primary leakage control is achieved by sealing the pins 50 to the housing by means of O-rings. As can be seen in the example of FIG. 2 the internal end of each pin 50 is surrounded by an O-ring 100.

The O-ring 100 is made of rubber and as can be seen in FIG. 2 is compressed in both lateral and axial directions. Axial constraint is provided by an axially facing shoulder 70 of the widened part 61 of the bore 60 and by an axially upwardly facing surface 71 of the flange 62. Lateral constraint is provided by a laterally outwardly facing surface 72 of the pin 50 and a laterally inwardly facing surface 73 of the widened part of the bore 60.

The unconstrained and unstressed form of the O-ring is shown in dotted lines in FIG. 2. It can be seen, therefore, that the O-ring is stressed and consequently leakage of electrolyte through the bore 61 is minimized even with variations in temperature and liquid pressure and other physical conditions since the O-ring remains in its stressed condition. The exact position of the O-ring 100 can be varied and for example it could be located downstream of the interference fit as opposed to upstream as shown in FIG. 2.

In the FIG. 2 example, the various components forming the seal assembly are separately manufactured and then connected together.

We have found that significant advantages can be achieved using a two-shot or three-shot injection moulding process.

Figure 3A:
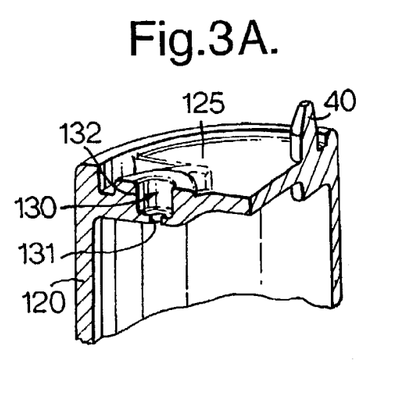
FIGS. 3A-3D are partial, perspective views of different stages in the fabrication of part of a gas sensor using a two-shot injection moulding process.
Figure 3B:
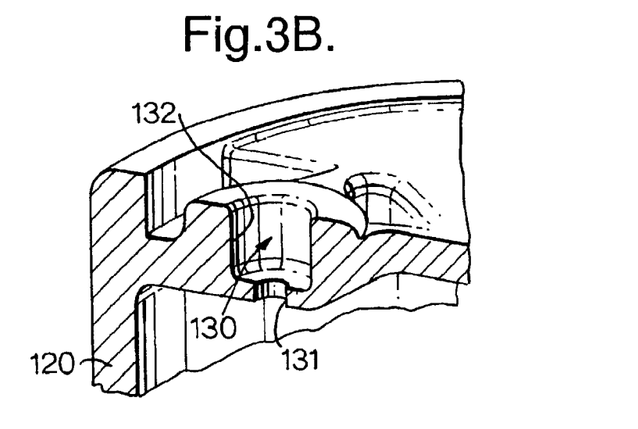

FIG. 3A illustrates part of a main housing moulding 120 similar to the housing 65 in FIG. 1. The housing moulding 120 is formed in a single injection moulding shot and includes a base 125, a dummy pin 40 and a bore 130 having a narrow section 131 and a widened section 132. The bore 130 can be seen more clearly in FIG. 3B.

Figure 3C:
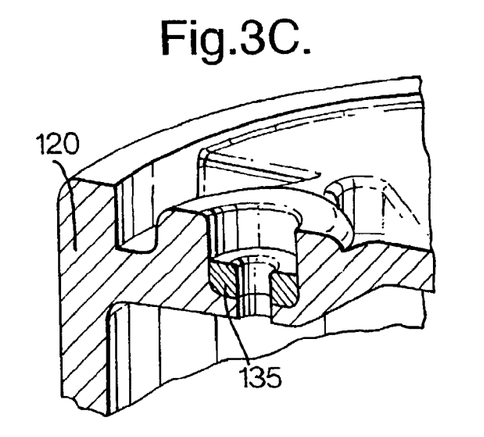
Figure 3D:
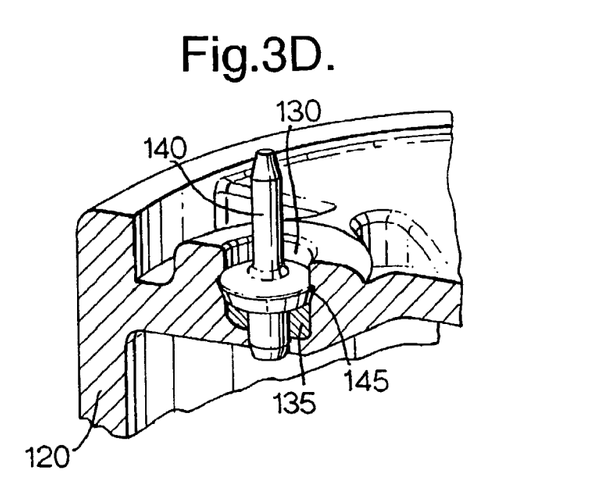
Figure 4A:
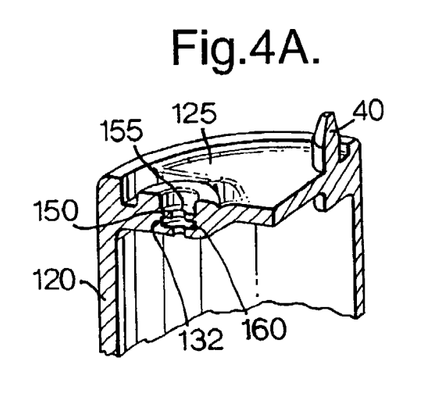
FIGS. 4A-4D are perspective views of part of another example of an electrochemical gas sensor housing during its fabrication using a two-shot injection moulding process.
Figure 4B:
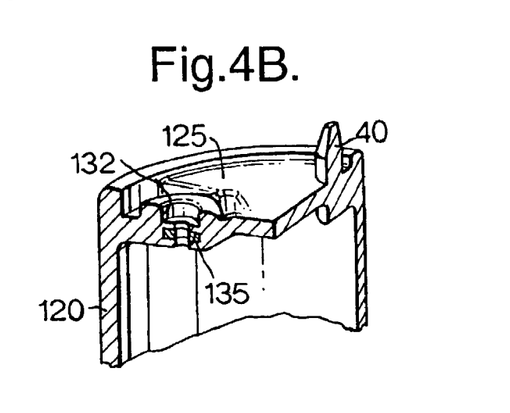
Figure 4C:
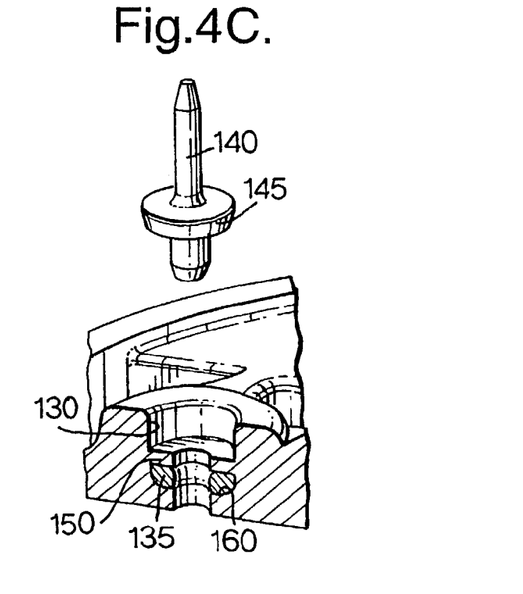
Figure 4D:
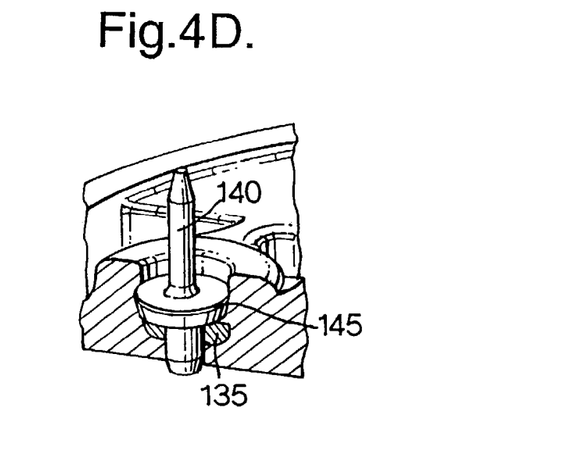

In a second injection moulding shot, a thermoplastic O-ring 135 is located in the base of the widened part 132 of the bore 130 to which it is both mechanically and chemically bonded (FIG. 3C). This produces a semi-constrained form of the seal which becomes fully constrained upon the introduction of a metal pin 140 (FIG. 3D) generating a seal between the pin and main polymer housing. The pin 140 is retained in position by a radial barb 145 as in the FIG. 2 example.

FIG. 4 illustrates an advantageous development of the FIG. 3 example. In this case, the bore 130 includes a radial flange 150 produced during the first moulding shot (FIG. 4A), the flange 150 having a central opening 155. In a second shot, a seal 135 is injected into the space defined between the flange 150 and the base 160 of the widened part 132 of the bore 130. In this design, the seal 135 is pre-constrained by this space into which it is moulded, again achieving both mechanical and chemical bonding to the base housing polymer. This means that the pin will always be fitted (FIGS. 4C and 4D) to a defined position therefore reducing the degree of variability in seal compression. In effect, the space in which the seal 135 is located defines a U-shaped recess surrounding the bore.

FIG. 5 illustrates a further development of the moulding process in which a three-shot process is used. Initially, a metal pin 140 is provided (FIG. 5A) as in the previous examples. This is loaded into mould tooling (not shown) and then in a first shot, a seal 160 is moulded around a flange 144 defining the barb 145 (FIG. 5B).

In a second shot (FIG. 5C), the main body of the housing 120 is injection moulded about the pin and seal thus defining the bore 130.

Finally, in a third shot (FIG. 5D), an external seal is moulded as shown at 170.

A variety of materials may be used for the different components providing they are compatible with each other and Table 1 below provides a list of thermoplastic materials and an indication of where they are compatible for good adhesion.

Typically, the housing 120 will be moulded from a polymer plastics material such as ABS while the seals 160,170 will be formed from thermoplastic elastomer materials (TPEs) or high flow polymers of which suitable examples are set out in Table 1.

Figure 5A:
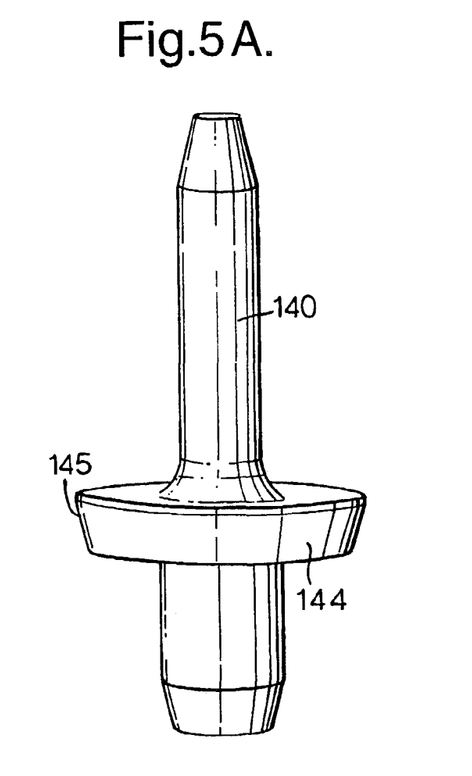
FIGS. 5A-5D are perspective views illustrating the fabrication of part of a further example of an electrochemical gas sensor using a three-shot injection moulding process; and, FIG. 6 illustrates cross-sections through four alternative annular seals.
Figure 5B:
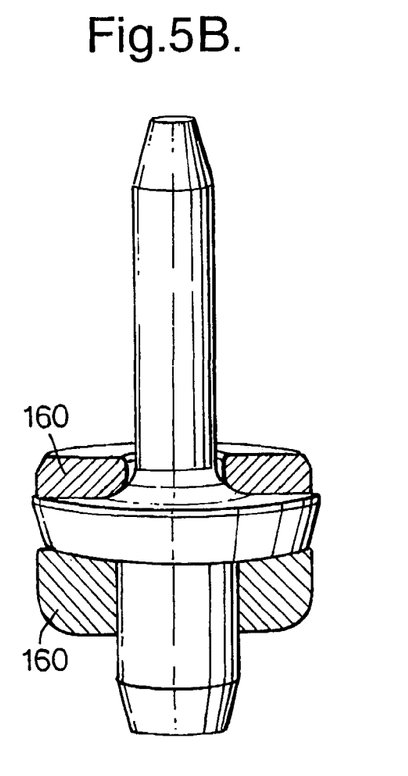
Figure 5C:
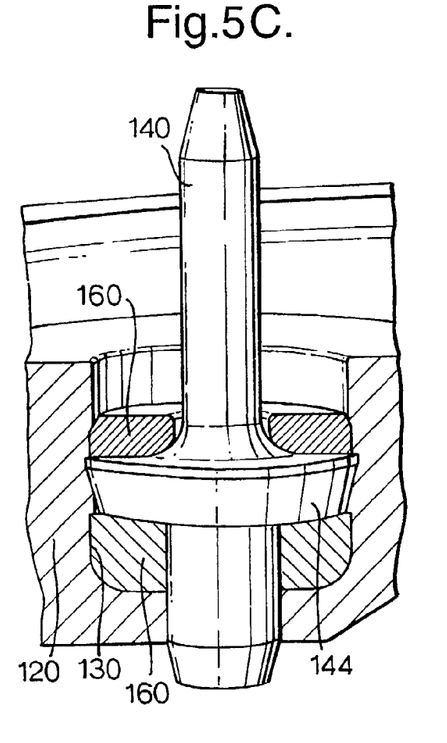
Figure 5D:
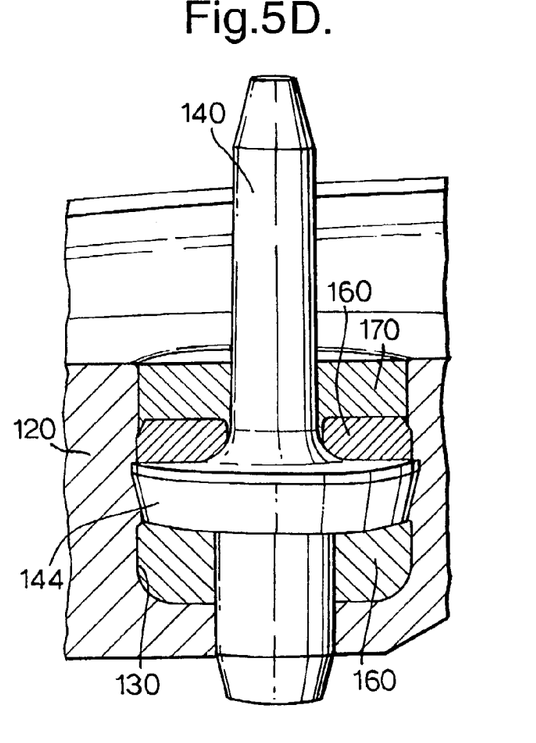

It will be appreciated that the FIG. 4 example could be modified such that in the first shot the seal 135 is moulded around the pin 140 and then the housing 120 is moulded around the seal in a similar way to the steps illustrated in FIGS. 5A-5C.

The two- and three-shot moulding processes are preferably carried out using a single tool although this is not essential.

Whilst the designs discussed above relate to the manufacture of an oxygen sensor, the design is not limited to sealing in the region of current collectors. Neither is it limited to oxygen sensors, but can also be used to generate the seals within any other areas of the gas sensor including toxic sensors, and indeed wherever an O-ring is currently employed.

Figure 6:
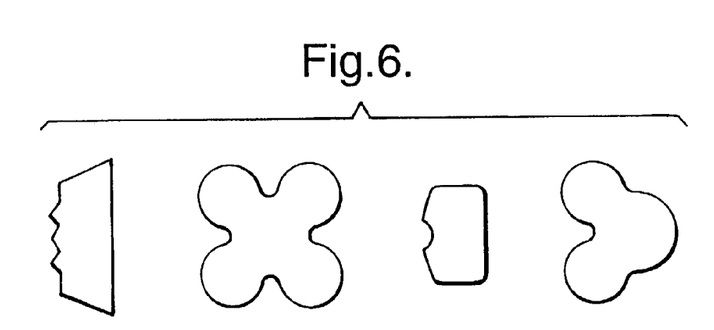

In addition, although the examples described above make use of conventional O-rings with circular cross-sections, a variety of other annular seals could be used. FIG. 6 illustrates cross-sections through four such examples which illustrate the wide variety of cross-sections applicable.

TABLE 1

Typical material adhesion combinations

| | Material Premolding | Thermoplastics |||||||||||||||||
|---|---|---|---|---|---|---|---|---|---|---|---|---|---|---|---|---|---|
| | | ABS | ASA | CA | EVA | PA 6 | PA 66 | PC | PE-HD | PE-LD | PMMA | POM | PP | PPO MOD | PS-GP | PS-HI | PBTP | TPU |
| Thermoplastics | ABS | + | + | + | + | + | + | + | − | − | + | − | − | − | ○ | ○ | + | + |
| | ASA | + | + | + | + | + | + | + | − | − | + | − | − | − | ○ | − | + | + |
| | CA | + | + | + | ○ | | | − | − | | − | − | − | − | − | − | + | + |
| | EVA | + | + | ○ | + | | | | + | + | | | + | | + | + | | |
| | PA 6 | + | + | | | + | + | + | ○ | ○ | | − | ○ | − | − | − | + | + |
| | PA 66 | + | + | | | + | + | ○ | ○ | ○ | | − | − | − | − | − | + | + |
| | PC | + | + | | | + | ○ | + | − | − | | − | − | − | − | − | + | + |
| | PE-HD | − | − | − | + | ○ | ○ | − | + | + | ○ | ○ | − | − | − | − | − | — |
| | PE-LD | − | − | − | + | ○ | ○ | − | + | + | ○ | ○ | + | − | ○ | − | − | − |
| | PMMA | + | + | | | | | ○ | | | + | ○ | − | − | − | − | − | |
| | POM | − | − | − | | − | − | − | ○ | ○ | | + | − | − | − | − | − | |
| | PP | − | − | − | + | ○ | − | − | − | + | ○ | − | + | − | − | − | − | − |
| | PPO MOD | − | − | − | | − | − | − | − | − | | − | − | + | + | + | − | − |
| | PPO MOD GTX | − | − | − | | − | − | − | − | − | | − | − | + | + | + | − | − |
| | PS-HI | ○ | − | − | + | − | − | − | − | − | | − | − | + | + | + | − | − |
| | PBTP | + | + | + | | + | + | + | − | − | | − | − | − | − | − | + | + |
| | TPU | + | + | + | | + | + | + | − | − | | − | − | − | − | − | + | + |
| | PVC-W | + | + | + | − | | | | − | − | + | − | − | − | − | − | + | + |
| | SAN | + | + | + | + | + | + | + | − | − | + | − | − | ○ | − | − | + | |
| | TPR | ○ | ○ | − | | − | − | − | ○ | ○ | | + | + | − | − | ○ | − | |
| | PETP PEI | + | + | | | | + | − | − | | − | − | − | − | − | − | + | |
| | PSU | + | + | | | | + | − | − | | − | − | − | − | − | − | + | |
| | BLEND PC-PBTP | + | + | | + | + | + | − | − | | + | − | − | − | − | − | + | + |
| | BLEND PC-ABS | + | + | | | + | + | + | − | − | | + | − | − | − | − | + | + |

TABLE 1-continued

Typical material adhesion combinations

| | |
|---|---|
| TPE | PP/EPDM |
| Elastmer | EPDM |
| | NR |
| | SBR |
| | LSR |

| | | Thermoplastics | | | | | | | Rigid/flexible bonds | | | | | | |
|---|---|---|---|---|---|---|---|---|---|---|---|---|---|---|---|
| | | | | | | | BLEND | BLEND | TPE | | | | | | |
| Material | | | | | | | PC- | PC- | | | PP/ | Elastomers | | | |
| | Premolding | PVC-W | SAN | TPR | PETP | PEI | PSU | PBTP | ABS | SEBS | TPU | EPDM | EPDM | NR | SBR | LSR |
| Thermoplastics | ABS | + | + | ○ | + | | + | + | + | + | + | | | | | |
| | ASA | + | + | ○ | + | | + | + | + | + | | | | | | |
| | CA | + | + | − | | | | | | | | | | | | |
| | EVA | − | + | | | | | | | | | | | | | |
| | PA 6 | | + | − | | | | + | + | + | + | + | | − | | |
| | PA 66 | | + | − | | | | + | + | + | + | + | | − | | |
| | PC | | + | − | + | | + | + | + | + | + | | | | | |
| | PE-HD | − | − | ○ | − | | − | − | − | | | | | | | |
| | PE-LD | − | − | ○ | − | | − | − | − | | | | | | | |
| | PMMA | + | + | − | | | | + | + | + | | | | | | |
| | POM | − | | − | | | − | − | | | | | | | | |
| | PP | − | − | + | | | − | − | − | + | − | + | | | | |
| | PPO MOD | − | ○ | + | − | | − | − | − | | | | | | | |
| | PPO MOD GTX | − | ○ | + | − | | − | − | − | | | | | | | |
| | PS-HI | − | − | ○ | − | | − | − | − | ○ | | | | | | |
| | PBTP | + | + | − | + | | + | + | + | + | | | | | | |
| | TPU | + | + | − | + | | + | + | | | | | | | | |
| | PVC-W | + | + | | | | | + | + | | | | | | | |
| | SAN | + | + | | | | | + | + | + | | | | | | |
| | TPR | | | + | − | | − | − | − | + | | | | | | |
| | PETP | | − | | + | | + | + | + | ○ | | | | | | |
| | PEI | | | | | + | − | | | | | | | | | |
| | PSU | | − | | + | | + | + | + | | | | | | | |
| | BLEND PC-PBTP | + | + | − | + | | + | + | + | + | | | | | | |
| | BLEND PC-ABS | + | + | − | + | | + | + | + | + | | | | | | |
| TPE | PP/EPDM | | | | | | | | | | | + | + | | | |
| Elastmer | EPDM | | | | | | | | | | | | + | | | |
| | NR | | | | | | | | | | | | | + | | |
| | SBR | | | | | | | | | | | | | | + | |
| | LSR | | | | | | | | | | | | | | | + |

+ Good adhesion
○ Bad adhesion
− No adhesion

The invention claimed is:

1. A method of sealing a gas sensor assembly comprising a housing; and an annular seal supported by the housing and defining a bore, the method comprising: molding the housing and seal in separate injection moulding shots: providing an elongate member including a laterally extending flange, the flange having a radial barb; inserting the elongate member into the bore so that the annular seal contacts a surface of the flange and an adjacent elongate portion of the member while the radial barb engages the bore so as to retain the member in position and to cause the seal to seal between the member and the housing, whereby the seal contacts the member so as to seal the bore against the passage of fluid, the annular seal being stressed in all lateral and axial directions.

2. A method according to claim 1, wherein the housing is moulded before the seal.

3. A method according to claim 1, wherein the seal is moulded around the member in a first shot; and the housing is moulded around the seal and member in a second shot.

4. A method according to claim 1, further comprising securing said member to the housing in sealing contact with the seal.

5. A method according to claim 1, wherein the seal comprises an O-ring.

6. A method according to claim 1, wherein the seal contacts part of the housing and the member so as to be restrained against movement in both lateral and both axial directions.

7. A method according to claim 6, wherein the seal is stressed in at least one of the lateral and axial directions.

8. A method according to claim 1, wherein the seal is located in an annular generally U-shaped recess opening into the housing and contacts opposed sides of the recess and the side of the recess opposite the member.

9. A method according to claim 8, wherein the opposed sides of the recess are substantially parallel and orthogonal to the side of the recess opposite the member.

10. A method according to claim 1, wherein the material of the housing is different from the material of the seal.

11. A method according to claim 1, wherein the seal is chemically bonded to the housing.

12. A method according to claim 1, wherein the member is elongate and sealed in a bore of the housing, further comprising moulding an additional seal into the bore in a third shot.

13. A method according to claim 1, wherein the member comprises an electrically conductive pin.

14. A method of manufacturing a gas sensor assembly comprising manufacturing a seal assembly having at least two electrically conductive pins by a method according to claim 13; and providing gas sensor components in the housing in electreal contact with the pins.

15. A method according to claim 14, wherein the components include sensing and counter electrodes, an intervening electrolyte located within the housing, and a gas access control member secured to the housing.

16. A method of manufacturing a seal assembly for a gas sensor assembly, the seal assembly comprising a housing; and an annular seal supported by the housing and defining a bore, the method comprising injection molding the housing about the seal; providing an elongate member including a laterally extending flange, the flange having a radial barb; inserting the elongate member into the bore so that the annular seal contacts a surface of the flange and an adjacent elongate portion of the member while the radial barb engages the bore so as to retain the member in position and to cause the seal to seal between the member and the housing, whereby the seal contacts the member so as to seal the bore against the passage of fluid, the annular seal being stressed in all lateral and axial directions.

17. A method according to claim 16, further comprising securing a member to the housing in sealing contact with the seal.

18. A method according to claim 16, wherein the seal comprises an O-ring.

19. A method according to any of claim 16, wherein the seal contacts parts of the housing and the member so as to be restrained against movement in both lateral and both axial directions.

20. A method according to claim 16, wherein the seal is stressed in at least one of the lateral and axial directions.

21. A method according to claim 16, wherein the seal is located in an annular, generally U-shaped recess opening into the housing and contacts opposed sides of the recess and the side of the recess opposite the member.

22. A method according to claim 21, wherein the opposed sides of the recess are substantially parallel and orthogonal to the side of the recess opposite the member.

23. A method according to claim 16, wherein the material of the housing is different from the material of the seal.

24. A method according to claim 16, wherein the seal is chemically bonded to the housing.

25. A method according to claim 16, wherein the member is elongate and sealed in a bore of the housing, further comprising moulding an additional seal into the bore in a third shot.

26. A method according to claim 16, wherein the member comprises an electrically conductive pin.

* * * * *